United States Patent
Al-Abbas et al.

(10) Patent No.: US 11,162,887 B2
(45) Date of Patent: Nov. 2, 2021

(54) APPARATUS FOR TANK BOTTOM SOIL SIDE CORROSION MONITORING

(71) Applicant: Saudi Arabian Oil Company, Dhahran (SA)

(72) Inventors: Faisal M. Al-Abbas, Dammam (SA); Mohammed Y. Salloum, Dammam (SA); Ala'a Edin M. Salameh, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 256 days.

(21) Appl. No.: 16/520,109

(22) Filed: Jul. 23, 2019

(65) Prior Publication Data

US 2021/0025808 A1  Jan. 28, 2021

(51) Int. Cl.
| | | |
|---|---|---|
| *G01R 27/08* | (2006.01) | |
| *G01N 17/00* | (2006.01) | |
| *F16L 58/10* | (2006.01) | |
| *G01B 7/06* | (2006.01) | |
| *G01N 17/04* | (2006.01) | |
| *G01N 27/04* | (2006.01) | |
| *G01N 17/02* | (2006.01) | |

(Continued)

(52) U.S. Cl.
CPC ........ *G01N 17/006* (2013.01); *F16L 58/1081* (2013.01); *G01B 7/06* (2013.01); *G01N 17/00* (2013.01); *G01N 17/02* (2013.01); *G01N 17/04* (2013.01); *G01N 17/043* (2013.01); *G01N 27/04* (2013.01); *G01N 27/041* (2013.01); *G01N 27/20* (2013.01); *G01N 33/383* (2013.01); *C23F 2213/32* (2013.01)

(58) Field of Classification Search
CPC ...... G01N 17/04; G01N 17/02; G01N 17/006; G01N 17/00; G01N 27/20; G01N 27/041; G01N 17/043; G01N 33/383; G01N 27/04; F16L 58/1081; G01B 7/06; C23F 2213/32

USPC .......... 324/76.11–76.83, 439, 459, 549, 600, 324/635, 644, 649, 662, 671, 691, 693, 324/699, 700, 716
See application file for complete search history.

(56) References Cited

U.S. PATENT DOCUMENTS

| | | |
|---|---|---|
| 4,238,298 A | 12/1980 | Tsuru et al. |
| 5,440,929 A | 8/1995 | Huang et al. |

(Continued)

FOREIGN PATENT DOCUMENTS

| | | |
|---|---|---|
| CN | 105891092 | 8/2016 |
| JP | H03160354 | 7/1991 |
| JP | 2006250823 | 9/2006 |

OTHER PUBLICATIONS

PCT International Search Report and Written Opinion in International Appln. No. PCT/US2020/042976, dated Nov. 10, 2020, 18 pages.

(Continued)

*Primary Examiner* — Raul J Rios Russo
(74) *Attorney, Agent, or Firm* — Fish & Richardson P.C.

(57) ABSTRACT

A metal plate corrosion sensing apparatus includes a conduit, and an electrical resistance probe mounted within the conduit, the electrical resistance probe configured to receive an electrical signal indicating a thickness of the metal plate, wherein the conduit comprises a plurality of slots configured to simulate an air/soil interface by permitting fluid access to the electrical resistance probe within the conduit through the slots.

20 Claims, 4 Drawing Sheets

(51) Int. Cl.
*G01N 27/20* (2006.01)
*G01N 33/38* (2006.01)

(56) References Cited

U.S. PATENT DOCUMENTS

| | | | |
|---|---|---|---|
| 5,627,749 A | 5/1997 | Waterman et al. | |
| 5,942,687 A | 8/1999 | Simmonds et al. | |
| 6,131,659 A | 10/2000 | Johnson | |
| 2002/0130780 A1* | 9/2002 | McQueen | G01F 1/6847 340/603 |
| 2012/0031188 A1* | 2/2012 | Dahlstrom | G01N 17/04 73/700 |
| 2019/0064095 A1* | 2/2019 | Clarke | G01R 27/02 |

OTHER PUBLICATIONS

"Electrical Resistance (ER) Probes," Cosasco, XP055745433, Jan. 2019, 3 pages.

Abed et al., "Evaluation of Impressed Current Cathodically Protected API 1 650 Tank Bottoms in the Presence of Vapor Phase Corrosion Inhibitor," NACE International Corrosion Conference Proceedings, NACE International, Jan. 2016, 11 pages.

Flitton et al., "Long Term Corrosion/Degradation Test Six Year Results," Idaho National Engineering and Environmental Laboratory, Sep. 2004, 226 pages.

Li et al., "Application of steel thin film electrical resistance sensor for in situ corrosion monitoring," Sensors and Actuators B: Chemical, Elsevier BV, NL, Dec. 2006, 120(2):368-377, 10 pages.

Tehada et al., "CPC Program Final Report Electrical Resistance Probe Corrosion Sensors for In-Situ Assessment for Waterfront Structures FY09 OSD Project F09NV04," Technical Report TR-NAVFAC-EXWC-CI-1301, Naval Facilities Engineering Command (NAVFAC), Engineering and Expeditionary Warfare Center, Feb. 2013, 46 pages.

Whited et al., "Mitigating Soil-Side Corrosion on Crude Oil Tank Bottoms Using Volatile Corrosion Inhibitors," Materials Performance, NACE International, XP055425787, Jun. 2013, 12 pages.

* cited by examiner

US 11,162,887 B2

APPARATUS FOR TANK BOTTOM SOIL SIDE CORROSION MONITORING

TECHNICAL FIELD

This disclosure relates to corrosion monitoring of metallic tanks.

BACKGROUND

Methods of using electrical readings for corrosion detection of metal plates are in use in petroleum, chemical processing, and other environments where on-line corrosion rate readings are required. Prior to carrying out these readings, in a laboratory environment, sample plates of the material to be evaluated for corrosion resistance are arranged on electrodes immersed in a medium substantially corresponding to the actual environment of the material during use. Small alternating current voltages of differing frequency are applied between the plates. The difference is determined between the peak voltages of the differing frequencies as converted from the currents flowing between both plates. This measurement provides the alternating current impedance of the corrosion reaction, which in turn gives an indication of the corrosion rate of the material in the medium being tested.

SUMMARY

The description relates to an apparatus for corrosion monitoring of a fluid tank at the generally inaccessible area under a tank floor. The apparatus can be used to calculate the corrosion rate of the fluid tank and the efficacy of any corrosion-prevention measurements in place. The structure of the apparatus provides on-site corrosion information about the bottom side of a tank in contact the ground (such as a sand bed) and with air pockets that generally form at the tank bottom/ground interface.

The apparatus has a corrosion sensor such as an electrical resistance (ER) probe that is mounted within a perforated or "slotted" conduit made of a nonmetallic, noncorrosive material such as polyvinyl chloride (PVC). The operating principle of ER probes is based on the change in resistance of the probe element as it is exposed to corrosive conditions. When encased in the slotted conduit, the probe more closely simulates the air gap between the tank floor and sand pad, providing a more accurate measurement of real life conditions. Applications include tank storage at oil and gas industry sites, power plants, desalination plants, and airports.

Typically, corrosion measurement tools that are used to measure the thickness of the tank plate from the product side to monitor corrosion are used during a turnaround, which involves a shutdown and cleaning of the system. Existing methods of corrosion calculation involve measuring the thickness of the tank plate from the product side (the inner, wetted side), rather than the soil side of the tank wall. The apparatus for corrosion monitoring describer here uses an ER probe that allows corrosion rate determination without probe removal and can be used in conductive systems as well as non-conductive environments such as oil, gas, and sand. The apparatus for corrosion measurement allows for online corrosion monitoring in the air environment for the soil side of tank floors, and not only from their top surfaces.

In some embodiments, a metal plate corrosion sensing apparatus includes a conduit; and an electrical resistance probe mounted within the conduit, the electrical resistance probe configured to receive an electrical signal indicating a thickness of the metal plate, wherein the conduit comprises a plurality of slots configured to simulate an air/soil interface by permitting fluid access to the electrical resistance probe within the conduit through the slots.

Implementations can include one or more of the following features: the conduit is a nonmetallic, non-corrosive material. The material is a polyvinyl chloride pipe. The plurality of slots are formed on a slotted portion at a first end of the conduit that surrounds and encloses a metal portion of the electrical resistance probe. A probe cover is attachable to an end of the conduit distant from the slotted portion of the conduit. The conduit is 1¼ inches in diameter and the slotted portion of the conduit is approximately one third of a total length of the conduit. The slots are 5-10 cm wide and set at intervals of 1-2 cm from each other. Connectors that connect the probe to a central processing unit that receives the signal indicating a thickness of the metal plate.

In some embodiments, a metal plate corrosion monitoring system includes at least one corrosion sensing apparatus including a conduit, and an electrical resistance probe mounted within the conduit, the electrical resistance probe configured to receive an electrical signal indicating a thickness of the metal plate, wherein the conduit comprises a plurality of slots configured to simulate an air/soil interface by permitting fluid access to the electrical resistance probe within the conduit through the slots, and a central processing unit in communication with the at least one corrosion sensing apparatus that receives the signal indicating a thickness of the metal plate.

Implementations can include one or more of the following features: the central processing unit is configured to execute instructions including receiving, from the at least one corrosion monitoring apparatus, a time series of electrical signals indicating the thickness of the metal plate, and determining a corrosion rate from the received signals. Determining a corrosion rate from the received signals includes plotting the time series of electrical signals, fitting a linear model to the time series, and calculating a slope from the linear model. The conduit is a nonmetallic, non-corrosive material. The material is a polyvinyl chloride pipe. The plurality of slots are formed on a slotted portion of the conduit that surrounds and encloses an active metal portion of electrical resistance probe. A probe cover is attachable to an end of the conduit distant from the slotted portion of the conduit. The conduit is 1¼ inches in diameter and the slotted portion of the conduit is approximately one third of a total length of the conduit. The slots are 5-10 cm wide and set at intervals of 1-2 cm from each other. The corrosion sensing apparatus is configured to measure the corrosion rate of the metal in contact with an air/soil interface.

In some implementations, a method of measuring corrosion rates of a metal plate includes measuring with at least one corrosion monitoring apparatus near an air/soil interface beneath the metal plate, the corrosion monitoring apparatus comprising: a linear conduit, and an electrical resistance probe mounted within the conduit, the electrical resistance probe configured to receive an electrical signal indicating a thickness of the metal plate, wherein the conduit comprises a plurality of slots configured to simulate an air/soil interface by permitting fluid access to the electrical resistance probe within the conduit through the slots, and receiving, at a central processing unit in communication with the at least one corrosion monitoring apparatus, a time series of electrical signals indicating the thickness of the metal plate, and determining a corrosion rate from the received signals. In some embodiments, determining a corrosion rate from the received signals includes fitting a linear model to a plot of the time series, and calculating a slope from the linear model.

This disclosure describes mounting the probes for corrosion sensing in a perforated slotted conduit that is connected into a central processing unit or equipped with a data logger to provide online corrosion monitoring for the soil-side corrosion of tank floors. The apparatus of this description is able to provide accurate, real-time monitoring of the corrosion rates locations under the tank floor where anti-corrosion techniques such as cathodic protection is not possible.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

Like reference symbols in the various drawings indicate like elements.

DETAILED DESCRIPTION

Figure 1A:
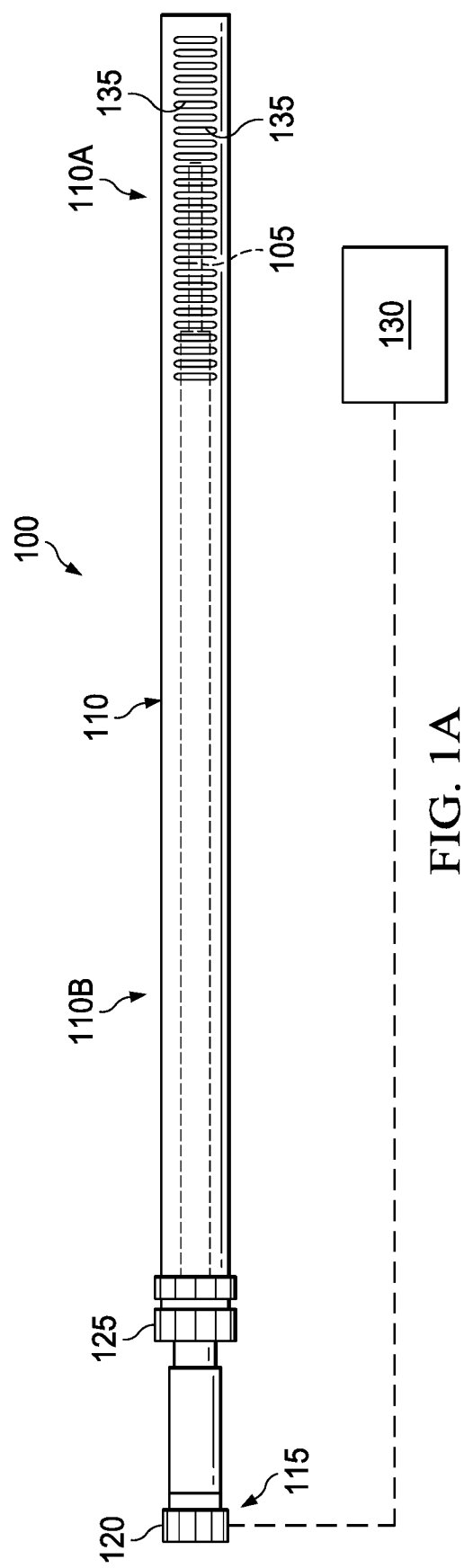
FIG. 1A is a schematic of a corrosion monitoring apparatus.

FIG. 1A shows a side view of a corrosion monitoring apparatus 100 suited for measuring and recording the corrosion levels in an inaccessible air gap under a liquid storage tank floor over extended periods. The apparatus 100 includes a corrosion sensing probe 105 such as an ER probe. ER probes determine metal loss from corrosion (or erosion) by measuring the electrical resistance of the metal element within the probe, which increases as the thickness or cross-section of the metal decreases. The metal element within the ER probe is generally freely exposed to the corrosive fluid and is compared to a reference element sealed within the probe body. With several readings taken over time, use of an ER probe allows engineers to plot metal loss as a function of time. The slope of the plotted curve represents the average corrosion rate over the selected interval. In general an ER probe has sensing elements made of the metal or alloy for which corrosion data is required. In some instances an ER probe body may be a thicker sample of the same material being measured, or be made of a less corrosive alloy than the material being measured.

The sensing probe 105 of the corrosion monitoring apparatus 100 is mounted within a protective sheath, being a linear perforated or slotted conduit 110. The slotted conduit 110 can be fabricated from any type of nonmetallic (that is, non-corrosive) material, such as a PVC pipe. The slotted conduit 110 may be slotted along its entire length, or can have a slotted portion 110A, and a non-slotted portion 110B. In a configuration with a non-slotted portion 110B, the slotted portion 110A surrounds and encloses the active metal portion of the sensing probe 105 (as shown in FIG. 1).

A removable probe cover 115 protects the end of the sensing probe 105 that is distant from the sensing probe 105 of the corrosion monitoring apparatus 100. The probe 105 runs through the center of the slotted conduit 110 along its length and is coupled together at connector 120, which can be a pipe coupling and reducer bushing for example. The connector 120 connects the sensing probe 105 to the rest of the slotted conduit 110 and centers the sensing probe 105 within the slotted conduit 110.

The slotted conduit 110 can be sized and shaped to ensure that the sensing probe 105 is near the area of the metal to be monitored. In one example, the slotted conduit 110 can be 850 centimeters (cm) long and 1¼ inch in diameter. The slotted portion 110A can be 250 cm long (or the entire length of the slotted conduit 110), or approximately one third of the total length of the slotted conduit. Slots 135 in the slotted portion 110A can be 5-10 cm wide and set at intervals of 1-2 cm. This configuration allows air to remain within the interior of the slotted conduit 110, as well as permitting liquid and some sand to trickle through. The slots 135 can be 0.5-1 cm long. In some instances the slots 135 are positioned only on a part of the slotted conduit 110 (for example, covering an arc of the surface of the slotted conduit 110 that is to be oriented up or oriented down when placed on-site). In other instances the slots 135 are positioned around the entire circumference of the slotted conduit 110; for example with two or more slots at each longitudinal position along the slotted conduit. The slots 135 can be radially symmetrically arranged in such an instance. The active sensing portion of the sensing probe 105 can be 25 cm long, and positioned such that its entire length is within the slotted portion 110A.

The corrosion monitoring apparatus 100 is electronically connected to a central processing unit 130 that reads and stores the readings from the sensing probe 105. The electronic connection can be wired, or wireless. Alternatively, the apparatus 100 can include a data storage device that can allow readings to be retrieved at a later time and once connected to a computer, downloaded for subsequent analysis.

Figure 1B:
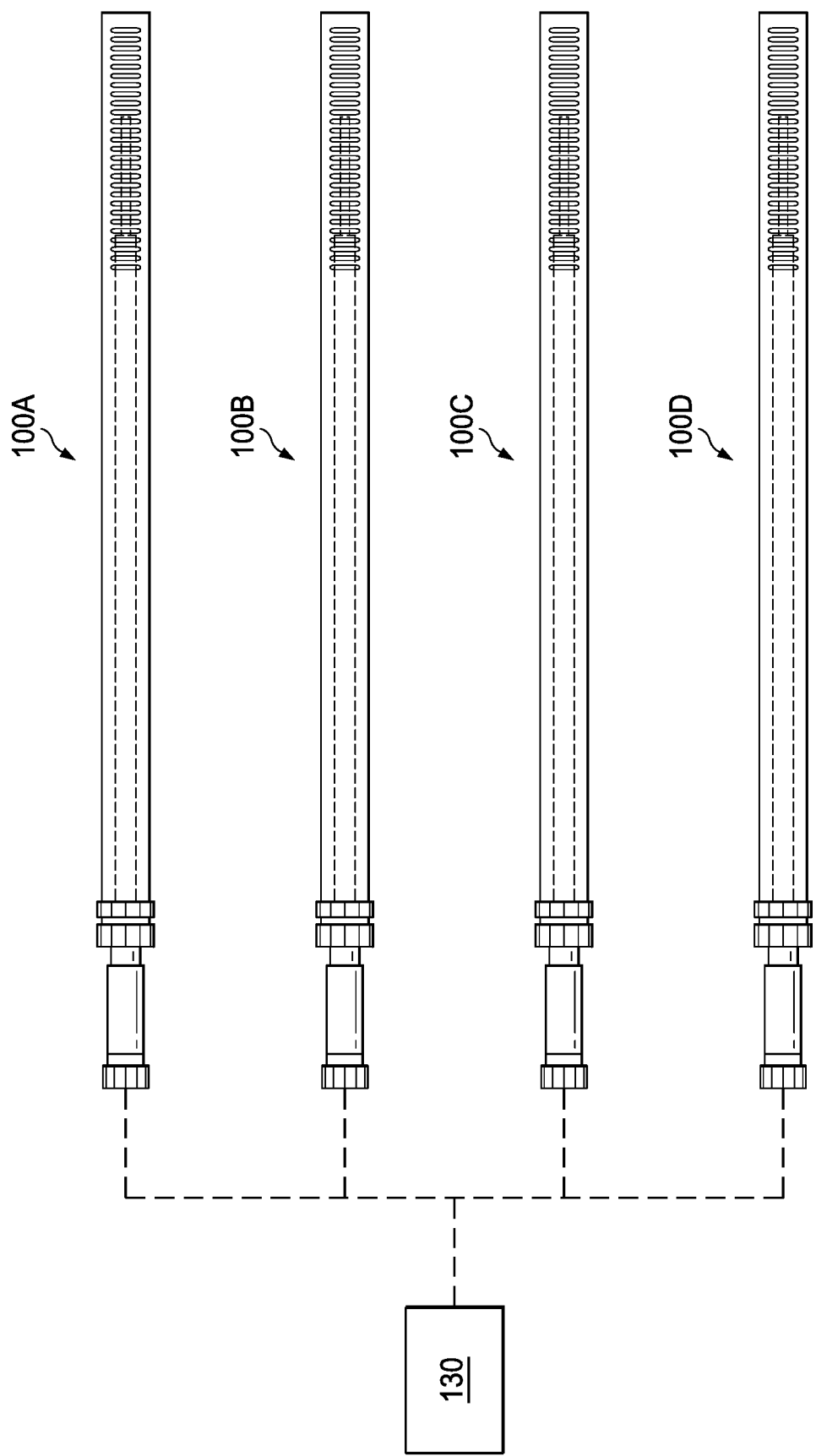
FIG. 1B is a schematic of a system using multiple corrosion monitoring apparatuses.

Referring to FIG. 1B, multiple corrosion monitoring apparatuses 100A, 100B, 100C, 100D can be used to take multiple readings while connected to the central processing unit 130. With such an arrangement, a user can measure and store corrosion data at multiple locations of a tank, or for several tanks. Although four corrosion monitoring apparatuses are shown, more than four corrosion monitoring apparatuses can be connected to a central processing unit 130.

Figure 2:
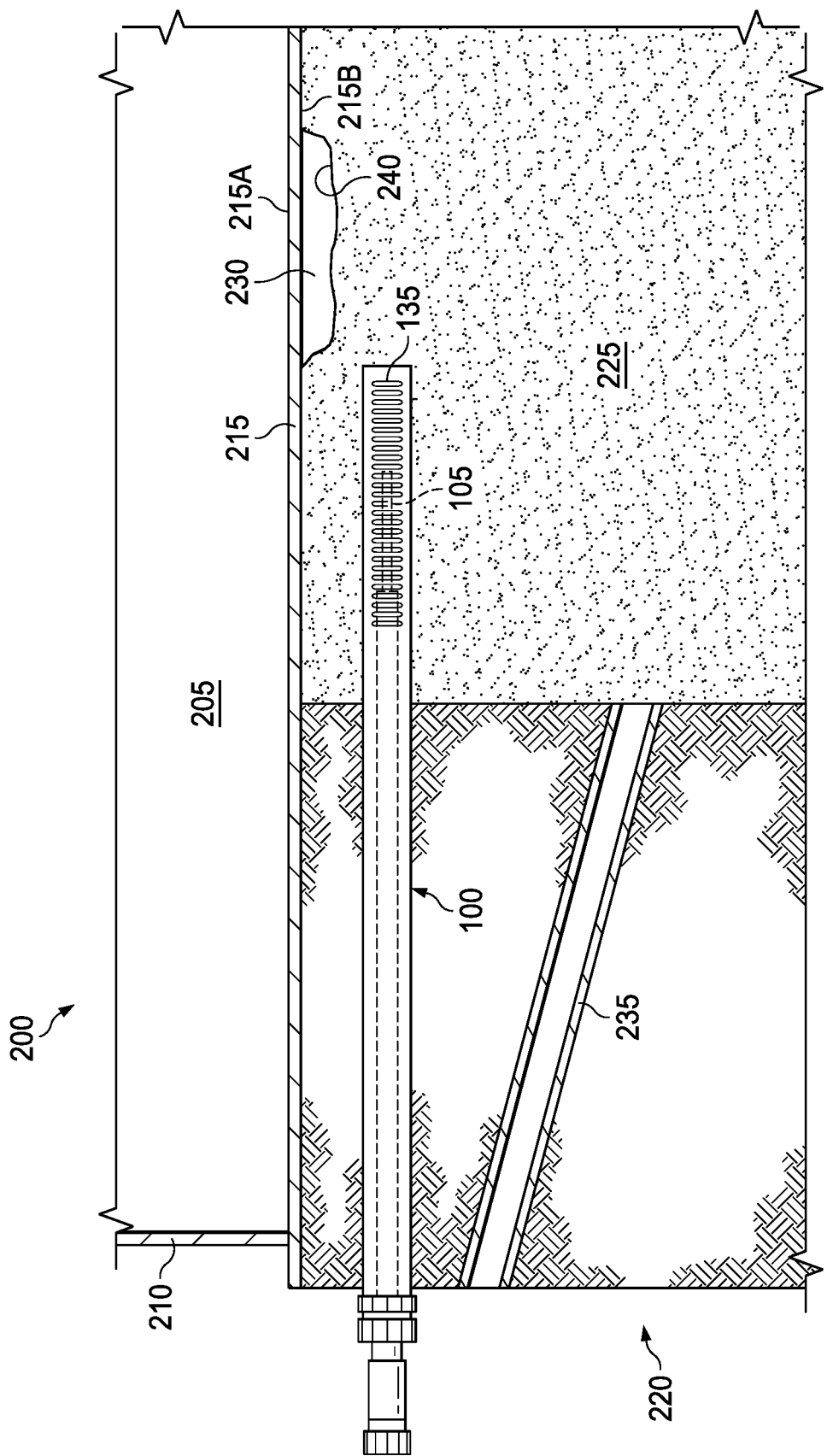
FIG. 2 is a schematic of a tank being monitored by the corrosion monitoring apparatus of FIG. 1.

FIG. 2 shows a cross section of an example use of a corrosion monitoring apparatus 100 at a tank site 200 that includes a tank 205 whose corrosion is to be monitored. The tank 205 includes a tanks shell 210, and a tank bottom plate 215. The tank bottom plate 215 is of primary interest, and rests on a ground surface 220 that can include sand 225. The tank bottom plate 215 has a tank side 215A that is in contact with the fluid within the tank 205, and a soil side surface 215B on the surface of the tank bottom plate 215 that is in contact with the ground 220 (including the sand 225). An air gap 230 generally forms between the soil side surface 215B of the tank bottom plate 215 and the top of the sand 225, forming an air/soil 240 interface in proximity to the soil side surface 215B.

The corrosion monitoring apparatus 100 is inserted beneath the tank bottom plate 215. For example, the corrosion monitoring apparatus can be positioned approximately 0.1-1 m from the surface of the ground 220. The slotted conduit 110 is inserted into the ground 220 so that the sensing probe 105 is beneath the tank bottom plate 215 (that is, inserted within the sand 225) and near the air/soil interface 240 beneath the tank bottom plate. The sensing probe 105 is inserted to be close as possible to the air gap 230 beneath the tank bottom plate to measure the corrosion rate in this area. The slots 135 of the corrosion monitoring apparatus 100 allow the sensing probe 105 within the conduit exposure to any fluid (gases and liquids) surrounding the exterior of the slotted conduit 110, but does not permit sand 225 (or permits only a limited amount of sand) to enter within the interior of the slotted conduit 110 and interact with the sensing probe 105. This arrangement simulates the air/soil interface 240 of the tank bottom plate 215.

The slotted conduit 110 can be inserted into the ground 220 so as to be oriented parallel to the tank bottom plate 215 as shown, or can be inserted at an angle. For example, the angle can be between 10 and 30 degrees. Also present in the tank site 200 is a cathodic protection access tube 235. The cathodic protection access tube 235 is positioned such that one end is near the ER probe cover 115 of the corrosion monitoring apparatus 100. The cathodic protection access tube 235 can be a PVC coated conduit.

To determine the corrosion rate as measured by the corrosion monitoring apparatus 100, metal loss data are collected using the setup shown in FIG. 2. Analysis of the collected data can take place on the central processing unit 130, or on another processor. The metal loss measurements are plotted as a function of time over the measurement period and transformed into a time series plot. A liner trend model is fitted to the time series plot, and the fit of the linear model can be checked using various accuracy measures and residual plots. Once a good linear model is confirmed, the corrosion rate is calculated using:

$$C=(M2-M1)/\Delta T \times 365$$

where M1 is the calculated metal loss at day 1 (according to the fitted trend line), M2 is the calculated metal loss at the last measurement day (according to the fitted trend line), $\Delta T$ is the time lapse between calculated metal loss M1 and M2 (in days), and C is the corrosion rate. Corrosion rate C is traditionally measured in mils per year (mpy), where a mil is a thousandth of an inch.

Figure 3:
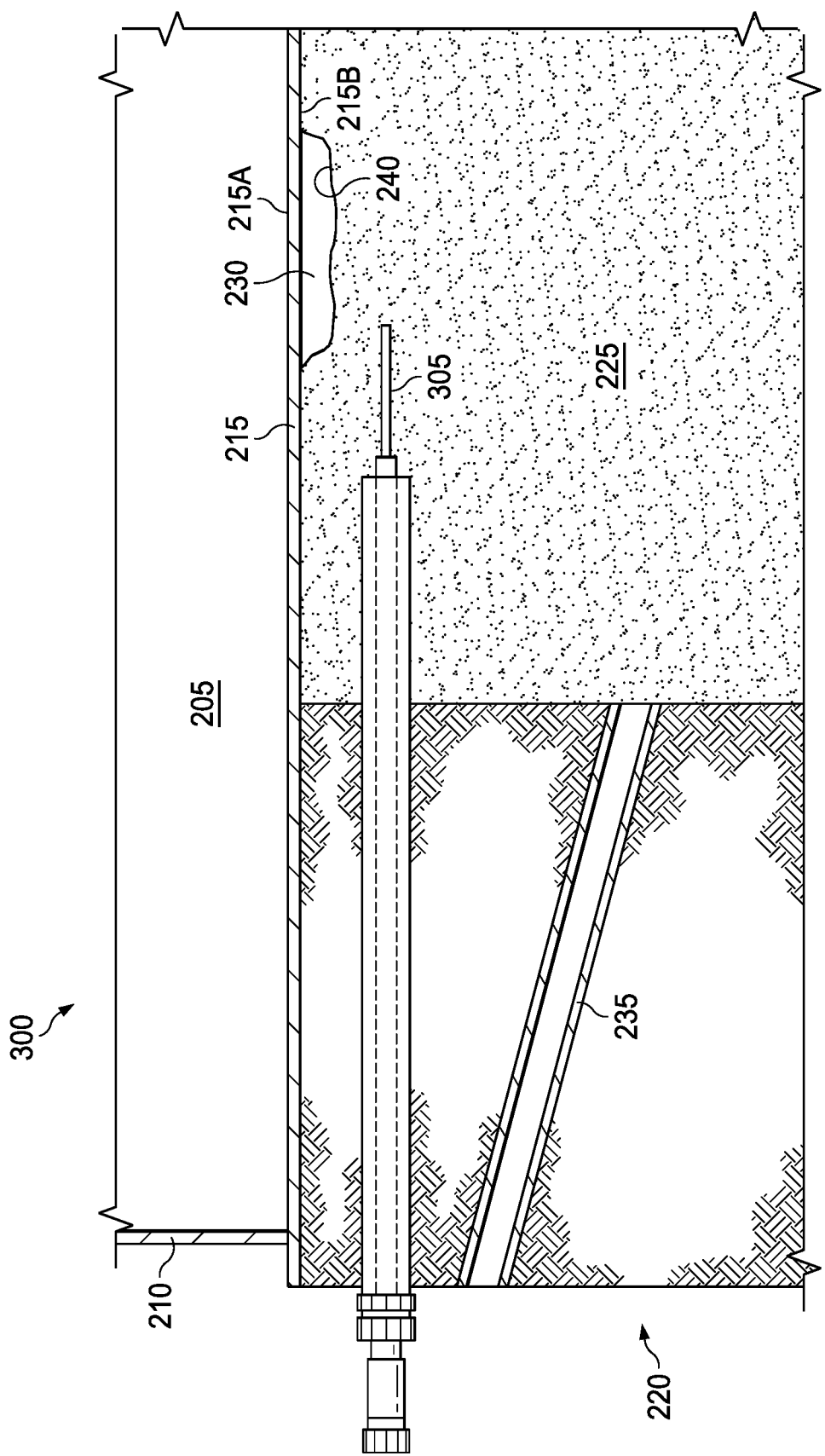
FIG. 3 is a schematic of a tank being monitored by a simple electrical resistance probe.

Referring to FIG. 3, a comparative experiment was carried out to evaluate the function of the corrosion monitoring apparatus 100 versus a traditional ER probe buried in sand. The overall experimental setup 300 is the same as the tank setup 200 shown in FIG. 2; however, in this instance a simple ER probe 305 was embedded in the sand 225 instead of a corrosion monitoring apparatus 100. Using the simple ER probe 305, metal loss data were recorded every hour over 30 days for the tank bottom plate 215. Time series plots were used to display collected data in chronological order and the trends for each of the two experimental simple ER probes 305 examined over time. The trends were generated by using a linear model as described above. The metal loss values at day one and day thirty were obtained from the fitted trend line and substituted into the equation for corrosion calculation.

The experimental results for the two tested simple ER probes 305 buried in sand 225 are shown in Table 1. The experiment returned an estimated corrosion rate of 1.55 mpy and 2.50 mpy, respectively, with an average of 1.99 mpy for the simple ER probes 305.

TABLE 1

| Probe | Trend line equation | M1 (mil) | M2 (mil) | $\Delta T$ (days) | C (mpy) |
|---|---|---|---|---|---|
| 305-1 | M = 1.65E−4 × (hr) + 4.58 | 4.58 | 4.70 | 30 | 1.55 |
| 305-2 | M = 2.83E−4 × (hr) + 5.26 | 5.26 | 5.47 | 30 | 2.50 |

The sample corrosion rate testing protocol was carried out for two corrosion monitoring apparatuses 100. The experimental setup is the same as shown in FIG. 2, which is the same as the setup shown in FIG. 3, with a corrosion monitoring apparatus 100 in place rather than a simple ER probe 305. Metal loss data were collected on an hourly basis for 30 days. The corrosion rate was determined using the approach outlined above.

Results of the experiment with the corrosion monitoring apparatus 100 are shown in Table 2. The corrosion monitoring apparatuses 100 showed higher corrosion rates, 4 mpy and 6.24 mpy, respectively, with an average of 5.12 mpy.

TABLE 2

| Probe | Trend line equation | M1 (mil) | M2 (mil) | $\Delta T$ (days) | C (mpy) |
|---|---|---|---|---|---|
| 100-1 | M = 7.05E−4 × (hr) + 5.4013 | 5.40 | 5.92 | 30 | 6.24 |
| 100-2 | M = 4.52E−4 × (hr) + 5.1093 | 5.11 | 5.44 | 30 | 4.00 |

The average corrosion rate of the simple ER probes 305 was 1.99 mpy whereas it was significantly higher at 5.12 mpy for the two corrosion monitoring apparatuses 100, an increase by a factor of more than 2.5. The variation is due to direct contact between the simple ER probe 305 with the sand 225. This arrangement of the corrosion monitoring apparatus 100 within the slotted conduit 110 prevents the sensing probe 105 of the corrosion monitoring apparatus 100 from touching the sand 225, and instead simulates the air gap 230 between the tank floor plate 215 and the sand 225. The corrosion monitoring apparatus 100 provides a more accurate evaluation of the corrosion rate, as it more closely reflects the actual conditions under which the tank bottom plate 215 is experiencing corrosive effects.

In a second experiment, the corrosion rate and efficacy of a corrosion control method using a corrosion inhibitor (deployed at the soil side surface 215B of the tank bottom plate 215) was evaluated. A corrosion inhibitor is a substance that prevents corrosion when it is added to the environment in small concentrations. Corrosion inhibitors can prevent corrosion by 1) adsorption, as a thin film on the surface of the corrosive metal, 2) laying down a thick anti-corrosive surface on the metal, 3) creating a passive surface on the surface of the metal, or 4) changing the environment by producing precipitates or by removing or disabling the media causing the corrosion.

In the second experiment, a corrosion inhibitor VpCI® (from Cortec®, Sweden) was injected into the air gap 230 between the bottom soil side surface 215B of the tank bottom plate 215 and the top of the sand 225. VpCI® is a vapor phase inhibitor that is transported via a vapor phase to surfaces of the metal surface to be protected, in this case the soil side surface 215B of the tank bottom plate 215. The vapor phase operates as a transport mechanism from the source to the soil side surface 215B of the tank bottom plate 215, where it builds up a layer of protection approximately one molecule thick, stopping the development of corrosion.

The corrosion rates were measured using the simple ER probes 305 and the corrosion monitoring apparatuses 100 following use of the corrosion inhibitor being injected into the air gap 230. Following the beginning of injection of the corrosion inhibitor, the simple ER probes 305 showed an average corrosion rate of 0.4 mpy, while the corrosion monitoring apparatuses 100 recorded average corrosion rate of 0.95 mpy. The corrosion monitoring apparatuses 100 again registered corrosion rates more than twice that of the simple ER probes 305, indicating a more accurate rate of corrosion.

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A metal plate corrosion sensing apparatus comprising:
   a conduit; and
   an electrical resistance probe mounted within the conduit, the electrical resistance probe configured to receive an electrical signal indicating a thickness of the metal plate, wherein the conduit comprises a plurality of slots configured to simulate an air/soil interface by permitting fluid access to the electrical resistance probe within the conduit through the slots.

2. The corrosion sensing apparatus of claim 1, wherein the conduit is a nonmetallic, non-corrosive material.

3. The corrosion sensing apparatus of claim 2, wherein the material is a polyvinyl chloride pipe.

4. The corrosion sensing apparatus of claim 1, wherein the plurality of slots are formed on a slotted portion at a first end of the conduit that surrounds and encloses a metal portion of the electrical resistance probe.

5. The corrosion sensing apparatus of claim 4, further comprising a probe cover attachable to an end of the conduit distant from the slotted portion of the conduit.

6. The corrosion sensing apparatus of claim 4, wherein the conduit is 1¼ inches in diameter and the slotted portion of the conduit is approximately one third of a total length of the conduit.

7. The corrosion sensing apparatus of claim 1, wherein the slots are 5-10 cm wide and set at intervals of 1-2 cm from each other.

8. The corrosion sensing apparatus of claim 1, further comprising connectors that connect the probe to a central processing unit that receives the signal indicating a thickness of the metal plate.

9. A metal plate corrosion monitoring system comprising:
   at least one corrosion sensing apparatus comprising:
      a conduit; and
      an electrical resistance probe mounted within the conduit, the electrical resistance probe configured to receive an electrical signal indicating a thickness of the metal plate, wherein the conduit comprises a plurality of slots configured to simulate an air/soil interface by permitting fluid access to the electrical resistance probe within the conduit through the slots, and
   a central processing unit in communication with the at least one corrosion sensing apparatus that receives the signal indicating a thickness of the metal plate.

10. The corrosion monitoring system of claim 9, wherein the central processing unit is configured to execute instructions comprising:
   receiving, from the at least one corrosion monitoring apparatus, a time series of electrical signals indicating the thickness of the metal plate; and
   determining a corrosion rate from the received signals.

11. The corrosion monitoring system of claim 10, wherein determining a corrosion rate from the received signals comprises:
   plotting the time series of electrical signals;
   fitting a linear model to the time series; and
   calculating a slope from the linear model.

12. The corrosion monitoring system of claim 9, wherein the conduit is a nonmetallic, non-corrosive material.

13. The corrosion monitoring system of claim 12, wherein the material is a polyvinyl chloride pipe.

14. The corrosion monitoring system of claim 9, wherein the plurality of slots are formed on a slotted portion of the conduit that surrounds and encloses an active metal portion of electrical resistance probe.

15. The corrosion monitoring system of claim 14, further comprising a probe cover attachable to an end of the conduit distant from the slotted portion of the conduit.

16. The corrosion monitoring system of claim 14, wherein the conduit is 1¼ inches in diameter and the slotted portion of the conduit is approximately one third of a total length of the conduit.

17. The corrosion monitoring system of claim 9, wherein the slots are 5-10 cm wide and set at intervals of 1-2 cm from each other.

18. The corrosion monitoring system of claim 9, wherein the corrosion sensing apparatus is configured to measure the corrosion rate of the metal in contact with an air/soil interface.

19. A method of measuring corrosion rates of a metal plate, the method comprising:
   measuring with at least one corrosion monitoring apparatus near an air/soil interface beneath the metal plate, the corrosion monitoring apparatus comprising:
      a linear conduit; and
      an electrical resistance probe mounted within the conduit, the electrical resistance probe configured to receive an electrical signal indicating a thickness of the metal plate, wherein the conduit comprises a plurality of slots configured to simulate an air/soil interface by permitting fluid access to the electrical resistance probe within the conduit through the slots, and
   receiving, at a central processing unit in communication with the at least one corrosion monitoring apparatus, a time series of electrical signals indicating the thickness of the metal plate; and
   determining a corrosion rate from the received signals.

20. The method of claim 19, wherein determining a corrosion rate from the received signals comprises, fitting a linear model to a plot of the time series, and calculating a slope from the linear model.

* * * * *